United States Patent
Gohl et al.

(10) Patent No.: US 7,902,497 B2
(45) Date of Patent: Mar. 8, 2011

(54) METHOD AND DEVICE FOR DETERMINING THE CONTENT OF LUBRICATING OIL IN AN EXHAUST GAS MIXTURE

(76) Inventors: Marcus Gohl, Escheburg (DE); Gerhard Matz, Buchholz (DE)

(*) Notice: Subject to any disclaimer, the term of this patent is extended or adjusted under 35 U.S.C. 154(b) by 511 days.

(21) Appl. No.: 10/584,926

(22) PCT Filed: Jan. 10, 2005

(86) PCT No.: PCT/EP2005/000140
§ 371 (c)(1),
(2), (4) Date: May 13, 2008

(87) PCT Pub. No.: WO2005/066605
PCT Pub. Date: Jul. 21, 2005

(65) Prior Publication Data
US 2008/0210855 A1 Sep. 4, 2008

(30) Foreign Application Priority Data

Jan. 9, 2004 (DE) .................. 10 2004 001 514

(51) Int. Cl.
*B01D 59/44* (2006.01)
*H01J 49/00* (2006.01)

(52) U.S. Cl. ......... 250/282; 250/281; 250/287; 250/288; 702/22; 702/23; 702/24

(58) Field of Classification Search .................. 250/281, 250/282, 287, 288; 702/22–24
See application file for complete search history.

(56) References Cited

U.S. PATENT DOCUMENTS

| 2,939,952 A | 6/1960 | Paul et al. |
| 5,420,425 A | 5/1995 | Bier et al. |
| 7,611,901 B2 * | 11/2009 | Fitamen et al. .................. 436/60 |

OTHER PUBLICATIONS

International Preliminary Report on Patentability dated Oct. 3, 2006, directed to counterpart international application PCT/EP2005/000140.
Blauth, Erich W. (1996). Chapter Section 5.3.2.1 "Dynamic mass spectrometers," *In Path-Stability Spectrometers*. Elsevier Publishing Company: New York City, NY. pp. 140-147.
Gohl et al. (2002). "Development and Application of a New Mass Spectrometer Based Measurement System for Fast Online Monitoring of Oil Emission in the Raw Exhaust Gas of Combustion Engines," *SAE Technical Paper Series*, Society of Automotive Engineers vol. 2002-01-2713, pp. 1-9.

* cited by examiner

*Primary Examiner* — Robert Kim
*Assistant Examiner* — Meenakshi S Sahu
(74) *Attorney, Agent, or Firm* — Morrison & Foerster LLP (57) ABSTRACT

The invention relates to a method for determining the lubrication oil content in an exhaust gas mixture comprising the steps of ionizing the exhaust gas mixture by means of an ion source (3), feeding the ions of the exhaust gas mixture to a filter unit (5) which is embodied as a multipole with a connected voltage source, setting a transmission range of the filter unit (5) according to a lubrication oil fraction to be measured, filtering out ions with a specific mass outside the transmission range and feeding the other ions to a measuring device (8) as well as measuring the intensity of the transmitted ions. According to the invention there is provision for the determination of the proportion of the lubrication oil fraction to be measured to be carried out as a global measurement of the intensity of the ions in a step over the transmission range. The invention also relates to a device for carrying out the method. The invention provides an improvement both in the measuring quality and in the measuring speed.

11 Claims, 5 Drawing Sheets

METHOD AND DEVICE FOR DETERMINING THE CONTENT OF LUBRICATING OIL IN AN EXHAUST GAS MIXTURE

The invention relates to a method for determining the lubrication oil content in an exhaust gas mixture comprising the steps of ionizing the molecules in the exhaust gas mixture by means of an ion source, feeding the ions of the exhaust gas mixture to a filter unit which is embodied as a multipole with a connected voltage source, setting a transmission range of the filter unit according to a lubrication oil fraction to be measured, filtering out ions with a specific mass outside the transmission range and feeding the other ions to a measuring device as well as measuring the intensity of the transmitted ions. The invention also relates to a determining device for carrying out the method, having an exhaust gas probe, an ion source which is connected via a measuring channel to a filter device and to a measuring device, the filter device being embodied as an electric multipole with a voltage source which is connected thereto and which is designed to generate a potential with a direct component and/or alternating component, and has a setting device for determining a transmission range according to a lubrication oil fraction to be measured.

The avoidance and reduction of emissions are assuming an ever more important role within increased efforts to protect the environment. For example, in the field of motor vehicle technology attempts are made not only to improve the emissions which originate from the combustion process which occurs in the engine but also to improve pollution which originates from secondary processes outside the actual combustion of the fuel. In the latter case, particularly lubrication oil emissions are significant. In order to be able to reduce them it is indispensable to be able to measure the lubrication oil emissions in the exhaust gas in order to produce and evaluate measures aimed at bringing about reduction.

Various measuring methods are known from public prior use. They are generally divided into two groups. The first group comprises conventional measuring methods for gravimetric or volumetric determination of the oil consumption, in which the lubricant balance is determined in the oil trough. In order to carry out gravimetric determination, the lubricant balance is calculated from the difference in weight before and after the running of the engine. The volumetric determination of the lubrication oil consumption is carried out using measuring rods or filling level sensors by means of the oil level in the crank casing sump. Surface movements, foaming of the oil and temperature-related changes in volume make the evaluation of the measurement results more difficult. A disadvantage is that the inclusion of fuel and combustion products can mean that the measured lubricant balance does not correctly reflect the lubricant consumption. Long measuring times (several hours per operating point), a high degree of measuring inaccuracy because of the very low oil consumption of modern engines and the lack of a possibility for sensing non-steady-state engine operating states are disadvantageous. Furthermore it is known to add easily detectable marking substances to the lubrication oil in a specific mixture ratio. In this measuring method, the measurements are carried out on the exhaust gas train. The difficulty with this measuring method is the selection of a suitable substance for marking. It must change the properties of the lubrication oil but must pass into the exhaust gas in proportion to the oil consumption irrespective of the operating state of the engine, and the marking proportion in the exhaust gas should be capable of being determined precisely even at low concentrations. Radioactive marking substances are very suitable. The ionizing radiation which they emit can be measured with a high degree of sensitivity. Selective marking of different fractions of the lubrication oil is made possible by substituting the hydrogen atoms of the lubrication oil with tritium. As a result, quantitative conclusions can be drawn about the consumption of individual fractions in the lubrication oil. Non-radioactive marking substances are, for example, sulfur, chlorine or pyrene. By means of a suitable measuring device the concentration of the marking substances in the exhaust gas is determined and the concentration of the lubrication oil is calculated therefrom by means of the known mixing ratio. These methods have the disadvantage that they are very complex, especially with respect to radioactive marking substances. The resolution of the measuring results over time is unsatisfactory.

Furthermore it is known (U.S. Pat. No. 2,939,952) to use a mass spectrometer as a measuring device. It is composed of an ion source, a filter device and a detector unit. The filter device is embodied, for example, as an electrical quadrupole to which a direct voltage source and an alternating voltage source are connected so that an electrical field which is periodic over time is produced in the filter. Owing to the field which is produced in the quadrupole, only ions with a certain specific mass m/e (specific mass/charge ratio) travel on stable paths and all the other ions are unstable and are eliminated by the filter. Given a specific absolute value ratio of the direct voltage to the alternating voltage with a fixed frequency and oscillation form of the alternating voltage the filter reaches its best selectivity level and permits precise resolution to one atom mass unit.

The application of the mass spectrometer for determining proportions of lubrication oil in exhaust gas has been proposed at the Powertrain and Fluid Systems Conference in San Diego, USA. The high resolution of the mass spectrometer makes it possible to determine the proportions of various components of the lubrication oil in the exhaust gas precisely as a function of their atomic weight. This is used to determine the proportion of specific groups such as, for example, the proportion of hydrocarbons with a high boiling point and masses between 170 to 550 atomic mass units. The method thus permits precise, fine-resolution and extremely quick measurement of individual fractions of the lubrication oil and its proportions in exhaust gas.

The invention is based on the object of providing a method and a device of the type mentioned at the beginning with which the abovementioned disadvantages are reduced.

The solution according to the invention lies in the features of the independent claims. Advantageous developments are the subject matter of the dependent claims.

According to the invention, there is provision, in a method for determining the lubrication oil content in an exhaust gas mixture comprising the steps of ionizing the molecules in the exhaust gas mixture by means of an ion source, feeding the ions of the exhaust gas mixture to a filter unit which is embodied as a multipole with a connected voltage source, setting a transmission range of the filter unit according to a lubrication oil fraction to be measured, filtering out ions with a specific mass outside the transmission range and feeding the other ions to a measuring device as well as measuring the intensity of the transmitted ions, for the determination of the proportion of the lubrication oil fraction to be measured to be carried out as a global measurement of the intensity of the ions in a step over the transmission range.

A number of terms used will be explained below:

Lubrication oil fraction is understood to mean groups of hydrocarbon compounds in the exhaust gas which originate from the lubrication oil.

Significant ions are understood to be ions whose consideration permits a representative conclusion to be drawn about the content of specific lubrication oil fractions in the exhaust gas. They extend over a certain range of molecular masses (amu) in the mass spectrum.

Specific mass is understood to be the mass/charge ratio (m/e).

A global measurement is understood to be a measurement which is carried out in one pass over the range. It is thus the opposite of a step by step individual measurement in which the individual measured values are determined discretely step by step over the range to be measured and added to form a sum value.

A transmission range of the filter device is a mass range which is defined by two limiting values, that is to say a range of ions with different specific masses m/e which the filter device transmits. The lower limiting value can be zero and the upper limiting value can be infinite.

The core of the invention is the idea that, instead of performing many individual measurements with subsequent addition of the individual values a global measurement is carried out over the range of the significant ions which originate from the desired lubrication oil fractions to be measured. The invention achieves this in that, of all of the entering ions of widely varying specific mass, all those ions whose specific mass is in the set transmission range (i.e. which lie in the desired transmission range) pass through the filter device and simultaneously arrive at the measuring device, while the other ions are stopped by the filter device. The simultaneous arrival of the transmitted ions at the measuring device produces a relatively strong measurement signal and the measuring speed is increased.

Since only one measurement has to be performed instead of a large number of measurements, the method according to the invention is significantly faster. If a realistic measuring time of 1 ms is assumed for a mass spectrometer such as is known from the prior art, this means that in a measuring range which extends, for example, from 50 to 500 atomic mass units (amu), the measuring time is 550 ms, that is to say over half a second. Thanks to the method according to the invention, only one measurement has to be carried out and the measuring time is therefore just 1 ms. This produces significantly improved dynamics which permit measurement in real time. The invention can thus advantageously be used for determining the emission behavior of an internal combustion engine. Thanks to the invention it is possible to determine the emission behavior in real time with respect to the crankshaft angle. It is thus possible to determine the phases in the working cycle from which the lubrication oil emissions originate. With the prior art it is not possible to acquire such information about the sequences.

The higher level of sensitivity of the invention with respect to low concentrations is due to the following. In the discrete step by step individual measurement according to the prior art, the measuring threshold has to be exceeded for each individual point of the measuring range because otherwise this point is not taken into account. In contrast, with the global measurement according to the invention all the ions which are transmitted (i.e. all those whose specific mass lies in the transmission range) arrive simultaneously at the measuring device. It is thus sufficient if the measuring threshold is exceeded over the range as a whole. As a result, for example in the case of a measuring range which comprises 500 atomic mass units, the sensitivity is improved by a factor of 500.

In a surprisingly simple way it is possible for the invention to achieve such a significant improvement in the measuring quality and measuring speed by ignoring the trend toward greater resolution which the prior art has pursued.

In a proven embodiment, the filter device is embodied as a quadrupole. It permits sufficiently precise selection together with good analytical calculation of its filter characteristic. The filter device is preferably actuated with a voltage source which generates a potential with a direct component and an alternating component. This makes it easily possible for the filter device to be selective for a certain mass range. This permits analytical calculation of the filter characteristic. The ratio of the absolute value of the direct voltage (U0) to the absolute value of the alternating voltage (V) is expediently preferably selected, with a preferably fixed frequency and oscillation form, to be equal to the ratio a/2q, where a is a selectable coefficient and the upper limiting mass is determined according to the equation $$m_1 = \frac{4 \cdot e \cdot V}{q_1 \cdot r_0^2 \cdot \omega^2}$$

and/or the lower limiting mass is determined according to the equation $$m_2 = \frac{4 \cdot e \cdot V}{q_2 \cdot r_0^2 \cdot \omega^2},$$

where $m_1 > m_2$.

The filter device is preferably operated as a bandpass filter but it can also be operated as a highpass filter—with a equal to zero. Of course, it is possible to provide not just one but also a plurality of quadrupoles which are possibly integrated into one another.

The invention also relates to a device according to the features of claim 7 et seq. for carrying out the method according to the invention. For an explanation, reference is made to the above statements and the following description of the figures.

The invention will be explained in more detail below with reference to the drawing in which an advantageous exemplary embodiment is illustrated in which.

Figure 1:
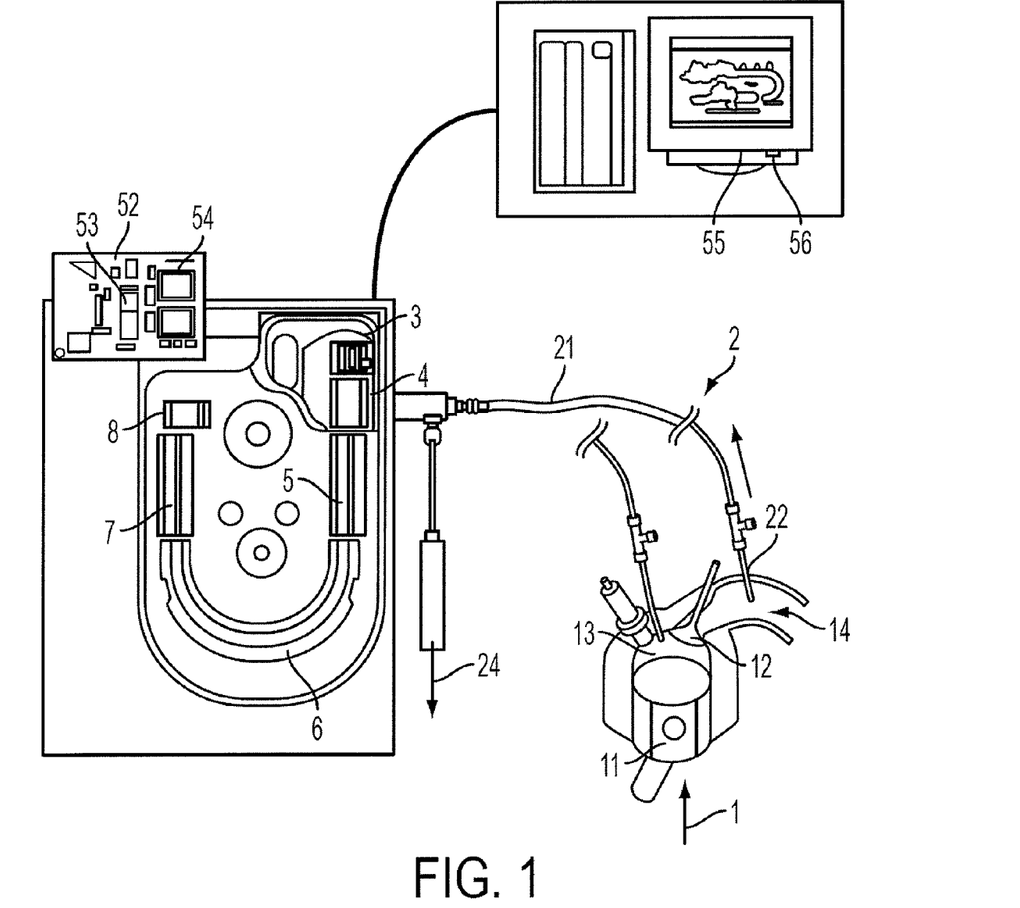
FIG. 1 shows a perspective view of a device for carrying out the method according to the invention.
Figure 2:
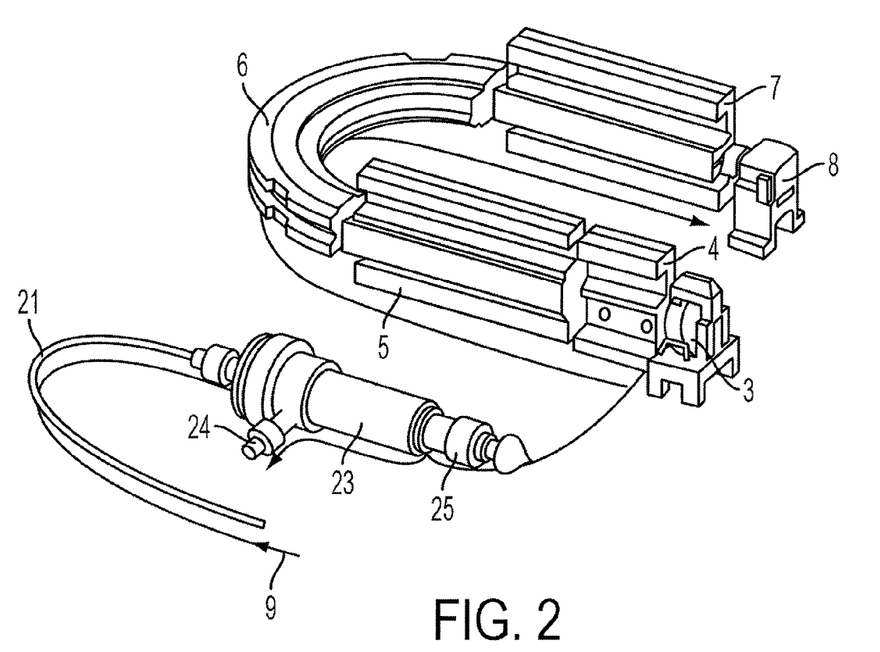
FIG. 2 shows a perspective view of a filter device.

An exemplary embodiment of a device according to the invention is illustrated in schematic form in FIGS. 1 and 2. It is explained with reference to the path taken by a stream of fluid to be analyzed through the device. This path is symbolized in FIG. 2 by a curved arrow 9.

The method according to the invention will be described below using the example of the measurement of exhaust gas in a spark ignition engine.

Figure 5:
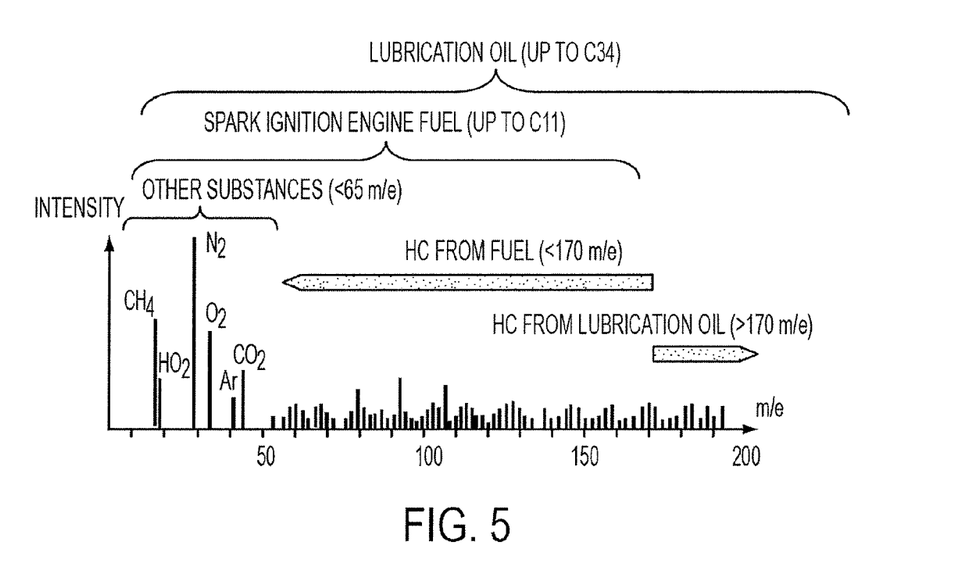
FIG. 5 is a schematic illustration of an EI mass spectrum of exhaust gas.

The exhaust gas of a spark ignition engine contains the following main components in an electron impact ionization (EI) mass spectrum (see FIG. 5):

1. Highly volatile exhaust gas components such as nitrogen, oxygen, carbon monoxide, carbon dioxide, water and argon. The ions of these components which are predominantly formed during electron impact ionization have a specific mass of for example N2=28 m/e, O2=32 m/e, CO=28 m/e, CO2=44 m/e, H2O=18 m/e and Ar=40 m/e. They thus lie in the range of <65 m/e.

2. Noncombustible hydrocarbons from the fuel which are composed of a maximum of 10 hydrocarbon atoms in spark ignition engine fuel. The resulting ions have a specific mass of <170 m/e.

3. Hydrocarbons from the lubrication oil which also generate ions of a specific mass of >170 m/e owing to the long-chain hydrocarbon groups of the lubrication oil (up to 36 hydrocarbon atoms).

The device according to the invention which is provided for carrying out the method comprises as main groups an ion source device 3, a prefilter 4, a first mass filter 5, a collision cell 6, a second mass filter 7 and a detector device 8. It is connected by means of an exhaust gas probe 2 to an exhaust train of an internal combustion engine (not illustrated) in order to determine lubrication oil emissions in the exhaust gas. The arrangement is explained below in more detail:

Exhaust gas which is emitted by the internal combustion engine 1 (a cylinder of the engine with piston 11, valve 12, combustion chamber 13 and exhaust gas manifold 14 are illustrated by way of example) is fed via the exhaust gas probe 2 with head 22 and a flexible transfer capillary 21 to an end side of a skimmer unit 25. The latter has at its side wall a vacuum port 24 for connection to a vacuum pump (not illustrated) in order to generate a preliminary vacuum which is necessary for the device to operate. The flexible transfer capillary 21 passes through the skimmer unit 23 and opens into a connecting head 25 which is arranged on its opposite end side. Said connecting head 25 is arranged on the ion source device 3 which is designed in such a way that the exhaust gas stream which flows in through the flexible transfer capillary 21 is ionized. The ionized source device is preferably configured in such a way that it can operate in various operating modes. A first operating mode is electron impact ionization (EI) and the second operating mode is chemical ionization (CI).

The preliminary filter 4 is arranged directly adjacent in the direction of flow of the exhaust gas stream 9. It is embodied as a hexapole and has the purpose of transferring the ions from the ion source into the high vacuum region of the mass filters 5, 7.

Figure 3:
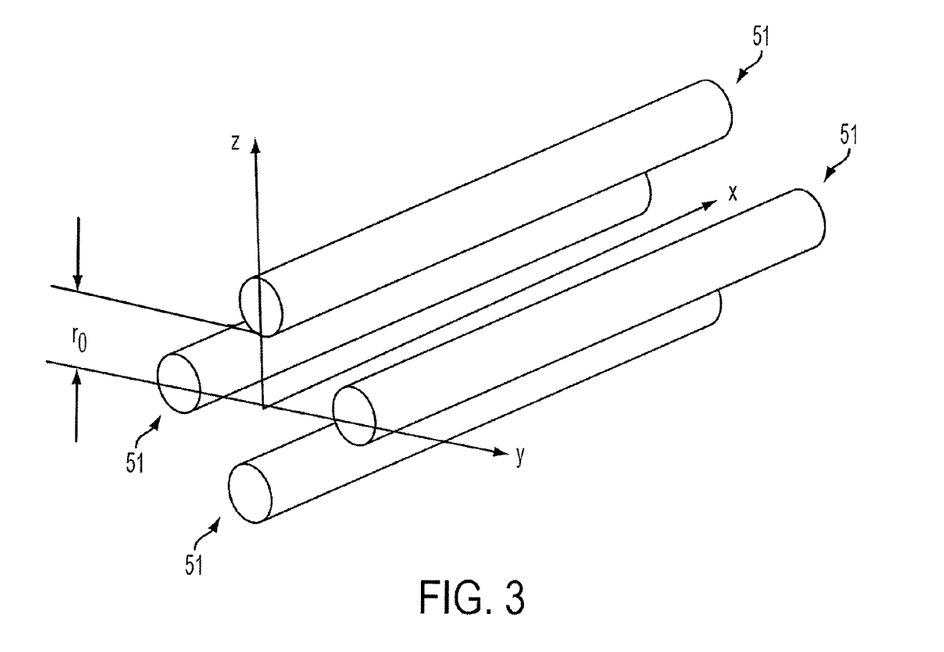
FIG. 3 shows a schematic view of a quadrupole.

Adjacent thereto, the first mass filter 5 is arranged, and behind it the second mass filter 7 after the collision cell 6. The mass filters 5, 7 are embodied as quadrupole filters. They serve the purpose of filtering out ions of undesired constituents. For example, for the purpose of measuring lubrication oil content the mass filters are set in such a way that ions from substances which are not associated with the lubrication oil (predominantly those with a lower specific mass than 170 amu) are extracted. The design of quadrupole filters in general is known from the prior art and does not need to be explained in more detail here. Particularly the following is important: the quadrupole filter is composed of at least one set of four rod-shaped electrodes 51 which are arranged parallel to one another extending in the x direction (see FIG. 3) at the corner points of a virtual quadrature in the y-z plane. The distance between the electrodes 51 and the center point of the virtual quadrature is r0. A voltage source 52 is connected to the electrodes in pairs. It has in each case a direct voltage module 53 and an alternating voltage module 54. The voltage which is emitted by the direct voltage module 53 is U0, and the voltage emitted by the alternating voltage module 54 is $V^* \cos(\omega^* t)$. Potentials which vary over time of the type $U0+V^*\cos(\omega^* t)$ are applied by means of the voltage source 52. This results in a field with cylindrical symmetry about the x axis according to the following equation:

$$\varphi = \frac{U_o + V \sin \omega t}{r_0^2} \cdot \frac{y^2 - z^2}{2}$$

If ions with the mass m and the charge e move in this field, the following movement equations apply to them $$\ddot{x} = 0$$
$$\ddot{y} - \left(\frac{2e}{m \cdot r_0^2}\right) \cdot (U_0 + V \cdot \cos\omega \cdot t) \cdot y = 0,$$
$$\ddot{z} + \left(\frac{2e}{m \cdot r_0^2}\right) \cdot (U_0 + V \cdot \cos\omega \cdot \tau) \cdot z = 0,$$

from which, by means of suitable substitution, the following equation system which is known as a Mathieu equation is obtained $$\frac{d^2 y}{d\xi^2} - (a + 2q \cdot \cos 2\xi) \cdot y = 0$$
$$\frac{d^2 z}{d\xi^2} + (a + 2q \cdot \cos 2\xi) \cdot z = 0$$

There are two types of solutions for the movement path of the ion for this equation system. Depending on the parameters a and q which describe the field, an ion either moves on a stable path or on an unstable path which leads to collision with an electrode. The resulting ranges of stability or instability are represented as a function of a and q in FIG. 4. If a fixed voltage ratio U0/V is selected, a straight line starting from the origin with the gradient a/q=2 U0/V=const describes the working range. A point on this straight line corresponds to each mass m. If the working straight line touches the stable region at its tip (straight line 1), the value qmax becomes 0.706 given a ratio of U0/V=0.166, and a maximum resolution is obtained. As a result, only a specific ion particle mass can pass through the quadrupole. Quadrupoles which are used as filters are usually set to this point of maximum selectivity.

In other words, the above means that given a predefined field the specific mass m/e of the ions alone determines whether the ion travels on a stable or unstable path. The quadrupole thus operates as a filter in a predefined field. In order to generate the field in a predefinable fashion, the voltage source 52 is provided. It comprises two actuating devices 55 and 56. The actuating device 55 serves the purpose of setting the level of the direct voltage amplitude, and the actuating device 56 serves the purpose of setting the level of the alternating voltage amplitude. The behavior of the quadrupole filter as a mass filter 5 can be set using the actuating devices 55 and 56. Various operating modes can be set.

Figure 4:
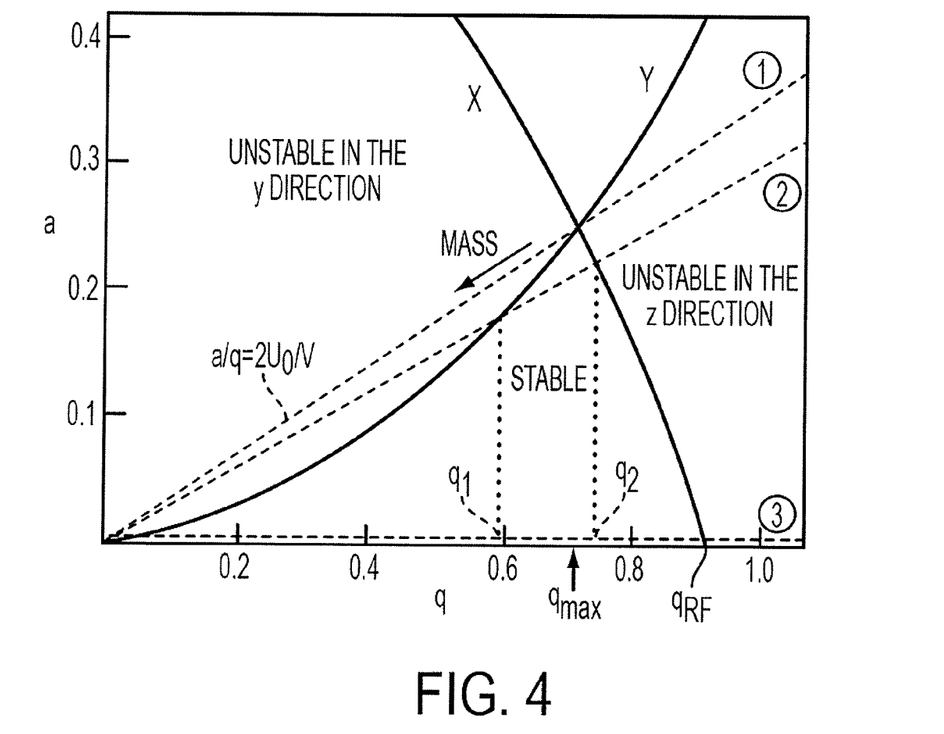
FIG. 4 is a characteristic curve diagram of various operating states.

In the "bandpass" operating mode, the lower limit q1 and the upper limit q2 of the mass range, through which the mass filter 5 allows ions to pass (see FIG. 4), are set using the two actuating devices 55, 56. The mass range of the ions which pass through the quadrupole on a stable path is determined by the upper limiting value $$\frac{m_1}{e} = \frac{4 \cdot V}{q_1 \cdot r_0^2 \cdot \omega^2}$$

and by the lower limiting value $$\frac{m_2}{e} = \frac{4 \cdot V}{q_2 \cdot r_0^2 \cdot \omega^2}$$

In the "highpass" operating mode, the sole (lower) limiting value mRF is set with the actuating devices. In this case, the parameter a=0 is selected, i.e. the direct voltage becomes zero and the quadrupole has a pure alternating field applied to it. The straight line 3 in FIG. 4 intersects the limiting line of the stable range only at one point, at qRF. This is calculated according to the following equation $$\frac{m_{RF}}{e} = \frac{4}{q_{RF} \cdot r_0^2} \cdot \frac{V}{\omega^2}$$

In the "bandpass" operating mode, all the ions whose mass lies within the two limiting masses in the set range pass through the mass filters 5 and 7. In the "highpass" operating range, all the ions with a specific mass greater than mRF/e pass through the quadrupole.

The detector device 8 is arranged in the direction of flow downstream of the mass filters 5, 7. It is designed to measure the ion stream flowing in through the mass filters 5, 7. It senses all the inflowing ions simultaneously. The measured values are transmitted to a suitable storage and output device such as a PC. A significantly improved signal is obtained by virtue of the fact that ions with different masses are sensed simultaneously.

The invention claimed is:

1. A method for determining the lubrication oil content in an exhaust gas mixture comprising the steps of ionizing the molecules in the exhaust gas mixture by an ion source, feeding the ions of the exhaust gas mixture to a filter unit comprising a multipole with a connected voltage source, setting a transmission range of the filter unit according to a lubrication oil fraction to be measured, filtering out ions with a specific mass outside the transmission range and feeding the other ions to a measuring device as well as measuring the concentration of the intensity of the transmitted ions,
wherein
the determination of the proportion of the lubrication oil fraction to be measured is carried out as a global measurement of the intensity of the ions in a single step over the transmission range.

2. The method as claimed in claim 1,
wherein
the filter unit is a quadrupole.

3. The method as claimed in claim 1 or 2,
wherein
the voltage source generates a potential with a direct component and alternating component.

4. The method as claimed in claim 3,
wherein
the ratio of the absolute value of the direct component to the absolute value of the alternating component is equal to the ratio a/2q, the upper limiting mass being determined according to the equation $$m_1 = \frac{4 \cdot e \cdot V}{q_1 \cdot r_0^2 \cdot \omega^2}$$

or the lower limiting mass being determined according to the equation $$m_2 = \frac{4 \cdot e \cdot V}{q_2 \cdot r_0^2 \cdot \omega^2},$$

wherein
a, q, $q_1$ and $q_2$ are selectable coefficients,
e is the charge of the transmitted ions,
V is the absolute value of the alternating component,
$r_0$ is the distance between the electrodes and center of the multipole,
$m_1$ is the upper limiting mass of the transmitted ions, and
$m_2$ is the lower limiting mass of the transmitted ions.

5. The method as claimed in claim 1 or 2,
wherein
the multipole is operated only with alternating voltage.

6. The method as claimed in claim 1 or 2,
wherein
the voltage which is connected to the multipole is selected such that the multipole is configured as a bandpass filter and has a first actuating device for a lower limiting mass and a second actuating device for an upper limiting mass of a transmission range.

7. A determining device for lubrication oil content in an exhaust gas mixture having an exhaust gas probe, an ion source which is connected via a measuring channel to a filter device and to a measuring device, the filter device comprising an electric multipole with a voltage source which is connected thereto and which is configured to generate a potential with a direct component or alternating component, and has a setting device for determining a transmission range according to a lubrication oil fraction to be measured,
wherein
the measuring device is a broadband measuring device which is configured to carry out the determination of the proportion of the lubrication oil fraction to be measured as a global measurement of the concentration of the molecules in a single step over the transmission range.

8. The device as claimed in claim 7,
wherein
the multipole is configured as a bandpass filter and has a first actuating device for a lower limiting mass and a second actuating device for an upper limiting mass of a transmission range.

9. The device as claimed in claim 8,
wherein
the multipole is configured as a highpass filter and has an actuating device for a lower limiting mass.

10. The device as claimed in claim 7, 8 or 9,
wherein
the filter device is configured to generate a potential with the direct component and the alternating component, and
the ratio of the absolute value of the direct component to the absolute value of the alternating component is equal to the ratio a/2q, the upper limiting mass being determined according to the relationship $$m_1 = \frac{4 \cdot e \cdot V}{q_1 \cdot r_0^2 \cdot \omega^2}$$

or the lower limiting mass being determined according to the equation $$m_2 = \frac{4 \cdot e \cdot V}{q_2 \cdot r_0^2 \cdot \omega^2},$$

with $m_1 > m_2$ being determined, and wherein
a, q, $q_1$ and $q_2$ are selectable coefficients,
e is the charge of the molecules within the transmission range,
V is the absolute value of the alternating component,
$r_0$ is the distance between the electrodes and center of the multipole, $m_1$ is the upper limiting mass of the molecules within the transmission range, and $m_2$ is the lower limiting mass of the molecules within the transmission range.

11. The device as claimed in claim 10, wherein
a is set to zero.

* * * * *

UNITED STATES PATENT AND TRADEMARK OFFICE
CERTIFICATE OF CORRECTION

PATENT NO. : 7,902,497 B2  Page 1 of 1
APPLICATION NO. : 10/584926
DATED : March 8, 2011
INVENTOR(S) : Marcus Gohl et al.

It is certified that error appears in the above-identified patent and that said Letters Patent is hereby corrected as shown below:

On the Title page, Under Section (30):

Please delete "10 2004 001 514" and add -- 10 2004 001 514.7 --

Signed and Sealed this
Thirty-first Day of May, 2011

David J. Kappos
*Director of the United States Patent and Trademark Office*